(12) United States Patent
Goddeeris et al.

(10) Patent No.: US 8,725,267 B2
(45) Date of Patent: May 13, 2014

(54) SIMULTANEOUS-SCRIPT EXECUTION

(75) Inventors: Frederic Goddeeris, Meerbeke (BE); Koen Van Herck, Kontich (BE)

(73) Assignee: Cochlear Limited, Macquarie University, NSW (AU)

( * ) Notice: Subject to any disclaimer, the term of this patent is extended or adjusted under 35 U.S.C. 154(b) by 44 days.

(21) Appl. No.: 13/438,984

(22) Filed: Apr. 4, 2012

(65) Prior Publication Data
US 2013/0268024 A1     Oct. 10, 2013

(51) Int. Cl.
*A61N 1/00*        (2006.01)
(52) U.S. Cl.
USPC .................................................. 607/57
(58) Field of Classification Search
USPC ......... 128/897–899; 600/379; 607/16, 55–59, 607/136–137
See application file for complete search history.

(56) References Cited

U.S. PATENT DOCUMENTS

2013/0090517 A1*  4/2013  Van den Heuvel et al. ..... 600/25

* cited by examiner

*Primary Examiner* — Christopher D Koharski
*Assistant Examiner* — Elizabeth K So
(74) *Attorney, Agent, or Firm* — McDonnell Boehnen Hulbert & Berghoff LLP

(57) ABSTRACT

The present application discloses systems and methods for engaging in a peer approach to script execution. In accordance with at least one embodiment of the disclosed systems and methods, a hearing prosthesis receives two scripts. Each script defines a different set of instructions to be carried out by the hearing prosthesis. In one embodiment, the command module receives one script and the stimulation module receives the other script. In such an embodiment, each module executes the script at substantially the same time. Furthermore, when one module encounters portions of the script that are somewhat time sensitive (e.g., a portion of a script that dictates to receive a transmission from the other module), the module will pause execution of the script and wait for execution of the other script to catch up.

6 Claims, 6 Drawing Sheets

---

Article of Manufacture 700

Program Instructions 702

- receiving at least two scripts, wherein each of the at least two received scripts defines a different set of instructions to be carried out by the medical prosthesis;

- simultaneously executing the at least two received scripts; and

- periodically pausing execution of one of the at least two scripts while execution of the other of the at least two scripts continues to execute Computer Readable Medium 703

Computer Recordable Medium 704

Article of Manufacture 700

Program Instructions 702

- receiving at least two scripts, wherein each of the at least two received scripts defines a different set of instructions to be carried out by the medical prosthesis;

- simultaneously executing the at least two received scripts; and

- periodically pausing execution of one of the at least two scripts while execution of the other of the at least two scripts continues to execute Computer Readable Medium 703

Computer Recordable Medium 704

FIG. 7

SIMULTANEOUS-SCRIPT EXECUTION

BACKGROUND

Various types of hearing prostheses may provide persons with different types of hearing loss with the ability to perceive sound. Hearing loss may be conductive, sensorineural, or some combination of both conductive and sensorineural hearing loss. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound, and a vibration mechanism to apply vibrations corresponding to the detected sound to a person's bone, thereby causing vibrations in the person's inner ear, thus bypassing the person's auditory canal and middle ear. Vibration-based hearing devices may include bone-anchored hearing devices, direct acoustic cochlear stimulation devices, or other vibration-based devices. A bone-anchored hearing device typically utilizes a surgically-implanted mechanism to transmit sound via direct vibrations of the skull. Similarly, a direct acoustic cochlear stimulation device typically utilizes a surgically-implanted mechanism to transmit sound via vibrations corresponding to sound waves to generate fluid motion in a person's inner ear. Other non-surgical vibration-based hearing devices may use similar vibration mechanisms to transmit sound via direct vibration of teeth or other cranial or facial bones.

Persons with certain forms of sensorineural hearing loss may benefit from cochlear implants and/or auditory brainstem implants. For example, cochlear implants may provide a person having sensorineural hearing loss with the ability to perceive sound by stimulating the person's auditory nerve via an array of electrodes implanted in the person's cochlea. The cochlear implant detects sound waves and converts them into a series of electrical stimulation signals that are delivered to the implant recipient's cochlea via the array of electrodes. Auditory brainstem implants may use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with sensorineural hearing loss to perceive sound.

The effectiveness of any of the above-described hearing prostheses depends not only on the design of the particular prosthesis but also on how well the device is configured for or "fitted" to a recipient. The process of "fitting" a hearing prosthesis with an appropriate set of configuration parameters (e.g., the operating instructions defining the particular manner in which the prosthesis detects acoustic signals and delivers responsive stimulation to the relevant portions of a person's outer ear, cranial or facial bones, teeth, middle ear, inner ear, cochlea, or brainstem) is often performed by an audiologist or other similarly-trained specialist typically in an office type setting or other professional setting away from the prosthesis recipient's home. It is generally advantageous to make this fitting process as efficient as possible.

SUMMARY

In accordance with at least some embodiments of the disclosed systems and methods, a hearing prosthesis receives two scripts. Each script defines a different set of instructions to be carried out by the hearing prosthesis. In one embodiment, the command module receives one script and the stimulation module receives the other script. In this embodiment, each module executes its script at substantially the same time. Furthermore, when one module encounters portions of its script that are somewhat time sensitive (e.g., a portion of a script that dictates to receive a transmission from the other module), the module will pause execution of the script and wait for execution of the other script to catch up.

BRIEF DESCRIPTION OF THE DRAWINGS

FIG. 7 shows an example of an article of manufacture including computer readable media with instructions for executing at least one script, according to an example embodiment.

DETAILED DESCRIPTION

Figure 1:
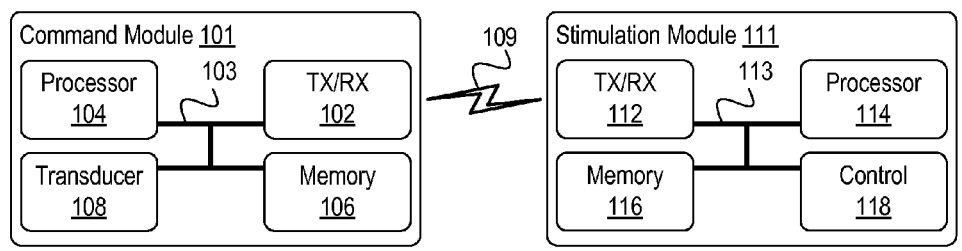
FIG. 1 shows a block diagram of certain selected hearing prosthesis components according to some embodiments of the disclosed systems and methods.

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

Certain aspects of the disclosed systems, methods, and articles of manufacture may be described herein with reference to hearing prosthesis embodiments and more particularly cochlear implant embodiments. However, the disclosed systems, methods, and articles of manufacture are not so limited. Many of the disclosed features and functions described with respect to the cochlear implant embodiments may be equally applicable to other embodiments that may include other types of medial stimulation prostheses including, prosthetic-limb stimulation devices, vibration-based hearing devices, direct acoustic stimulation devices, auditory brain stem implants, or any other type of medical stimulation prosthesis that is configured such that one component generates commands and transmits the commands across a data link to another component, which applies or executes the commands.

Before a hearing prosthesis recipient uses a hearing prosthesis, and perhaps at other times, an audiologist (or other entity) conducts a series of tests at what are known as "fitting sessions." These fitting sessions enable the audiologist to equip the hearing prosthesis with an appropriate set of configuration data that is customized to the recipient. Generally, the configuration data instructs the hearing prosthesis how to apply stimulation signals to the recipient.

Generally, a hearing prosthesis has two modules: a command module, which often includes a sound processor, and a stimulation module, which, in at least one embodiment, includes an array of electrodes implanted in the recipient's cochlea. To facilitate the series of tests, the command module is typically provisioned with a script. A script dictates several actions that the audiologist desires the hearing prosthesis to carry out. The command module executes the script and instructs the stimulation module to carry out certain test stimulations at appropriate times. This approach is referred to as the "master-slave" approach.

In some situations, the master-slave approach can be somewhat problematic because it involves frequent transmissions from the command module to the stimulation module. Such frequent transmissions can often result in a misalignment between command module timing and stimulation module timing. Therefore, to avoid a potential misalignment, the master-slave approach typically includes complex and time-consuming synchronization commands. However, these synchronization commands ultimately interfere with the test and usually result in a slower overall test. The present application discloses systems and methods to address these problems.

Example Hearing Prosthesis Configuration

FIG. 1 shows a block diagram of an example hearing prosthesis 100 according to some embodiments of the disclosed systems and methods. In some embodiments, hearing prosthesis 100 is a cochlear implant; however, in other embodiments, hearing prosthesis 100 is another kind of implant, such as a vibration-based hearing device, a direct acoustic stimulation device, or an auditory brain stem implant. The hearing prosthesis shown in FIG. 1 may be implanted into a hearing prosthesis recipient according to any general implant procedure. In some embodiments, hearing prostheses, such as hearing prosthesis 100, have additional or different components than those depicted in FIG. 1; but, for brevity's sake, the configuration depicted in FIG. 1 focuses on a selected set of components that may be helpful to illustrate certain aspects of the disclosed embodiments.

In the embodiment shown in FIG. 1, hearing prosthesis 100 includes a command module 101 and a stimulation module 111. Although not shown in FIG. 1, in some embodiments, the command module 100 is included within an external component assembly that is directly or indirectly attached to the body of the hearing prosthesis recipient, whereas the stimulation module 111 is included within an internal component assembly that is temporarily or permanently implanted in the hearing prosthesis recipient. However, in other embodiments, the command module 100 and the stimulation module 111 are both included within one or more internal component assemblies, each of which are temporarily or permanently implanted in the hearing prosthesis recipient.

The command module 101 is shown as including a transmit/receive sub-module 102, a processor sub-module 104, a memory sub-module 106, and a transducer sub-module 108, all of which may be connected directly or indirectly via circuitry 103. Similarly, the stimulation module 111 is shown as including a transmit/receive sub-module 112, a processor sub-module 114, a memory sub-module 116, and a control sub-module 118, all of which may be connected directly or indirectly via circuitry 113. In some embodiments, the sub-modules of the command module 101 are located on a single integrated circuit, whereas in other embodiments, the sub-modules of the command module 101 are spread out across two or more integrated circuits. Likewise, in some embodiments, the sub-modules of the stimulation module 111 are located on a single integrated circuit, whereas in other embodiments, the sub-modules of the stimulation module are spread out across two or more integrated circuits.

In the embodiment shown in FIG. 1, transducer 108 is configured to detect sound waves and generate an audio signal representative of those sound waves. Transducer 108 may be further configured to transmit to processor 104, via circuitry 103, a generated audio signal that is based on the detected sound waves. Depending on the desired configuration, transducer 108 may be one or more microphones, one or more telecoil induction pickup coils, or some other sound-detection device now known or later developed.

In the embodiment shown in FIG. 1, processor 104 is configured to receive, analyze, and encode an audio signal sent from transducer 108 (or another source) into one or more stimulation commands according to a particular sound-coding strategy. Processor 104 may also be configured to conduct one or more hearing prosthesis system diagnostic tests, analyze the results of the one or more hearing prosthesis system diagnostic tests, and/or implement one or more actions in response to the results of the one or more hearing prosthesis system diagnostic tests. In some embodiments, processor 104 may also be configured to analyze measured responses to stimulation signals generated via the electrodes of the hearing prosthesis 100. Depending on the desired configuration, processor 104 may include one or more processors, including but not limited to, programmable processors, application specific integrated circuits, programmable logic arrays, digital signal processors, and/or other general and/or special purpose processors configured to perform one or more of the functions of the hearing prosthesis 100 as described further below.

In the embodiment shown in FIG. 1, the transmit/receive sub-module 102 is configured to transmit stimulation commands produced by processor 104 to the stimulation module 111. In addition, the transmit/receive sub-module 102 is also configured to send other transmissions to the stimulation module 111, such as instructions to carry out one or more hearing prosthesis diagnostic tests, or any other type of transmission. Such transmission is carried out by way of data link 109 and may be of any protocol or format. In some embodiments, transmit/receive sub-module 102 includes a coil of a transcutaneous energy transfer system along with associated circuitry to drive the coil. However, in other embodiments, transmit/receive module 102 may be any radio-frequency (RF) interface or other wired or wireless communication interface that facilitates data communications.

As a general matter, data link 109 may be any coupling that enables data transmission between the transmit/receive sub-module 102 and the transmit/receive module 112. In some embodiments, data link 109 is a transcutaneous RF inductive link. In other embodiments, data link 109 is any air interface or other wired connection. Typically, data link 109 is a half-duplex data link. A half-duplex data link is a data link across which the command module 101 and the stimulation module 111 do not simultaneously transmit packets. Although, in other embodiments, data link 109 is a full-duplex data link. A full-duplex data link is a data link across which the command module 101 and the stimulation module 111 may simultaneously transmit packets.

In addition to communicatively coupling to transmit/receive sub-module 112, transmit/receive sub-module 102 may communicatively couple to an external fitting system (described below with respect to FIG. 2) by way of another data link. The transmit/receive sub-module 102 may be configured to send and/or receive information to and/or from the fitting system. For example, in some embodiments, the transmit/receive sub-module 102 is configured to receive configuration or map data from a fitting system. The transmit/receive sub-module 102 may also be configured to send measurement data to the fitting system. In some embodiments, the transmit/receive sub-module 102 may also be configured to send and/or receive data to/from other ancillary devices that are associated with the hearing prosthesis 100.

In the embodiment shown in FIG. 1, memory module 106 includes one or more computer-readable storage media that can be read from, written to, or otherwise accessed by processor 104. Moreover, the storage media of memory 106 is also configured to be read from, written to, or otherwise accessed by one or more of the transmit/receive sub-module 102 and/or the transducer 108. In some embodiments, the storage media in the memory sub-module 106 is configured to store configuration, or MAP, data for the hearing prosthesis 100 or other programming instructions that facilitate general operation of the hearing prosthesis 100 in accordance with the functions described herein. The storage media of the memory sub-module 106 may also be configured to store the results of one or more diagnostic tests that are initiated, performed, or otherwise controlled in whole or in part by either processor 104, the stimulation module 111, or a fitting system, such as the one described herein with respect to FIG. 2.

The hearing prosthesis 100 shown in FIG. 1 also includes a stimulation module 111, which generally includes functionality similar to that of the command module 101. For instance, stimulation module 111 includes a transmit/receive sub-module 112, which includes functionality similar to that of transmit/receive sub-module 102. In some embodiments, the transmit/receive sub-module 112 may be configured to receive over the data link 109 stimulation commands or other types of data transmitted by command module 101. Depending on the configuration, the transmit/receive sub-module 112 may be the counterpart of transmit/receive sub-module 102 insofar as transmit/receive sub-module 112 may include an internal coil of the noted transcutaneous energy transfer system. In some embodiments, however, transmit/receive sub-module 112 may be any RF interface or other wired or wireless communication interface that facilitates data communications.

Similar to processor 104, processor 114 may include one or more processors, including but not limited to, programmable processors, application specific integrated circuits, programmable logic arrays, digital signal processors, and/or other general and/or special purpose processors configured to perform one or more of the functions of the hearing prosthesis 100, such as operating control sub-module 118, as described further below.

In general, the arrangement of transmit/receive sub-modules 102 and 112, as depicted in this embodiment, operates to exchange messages between processor 104 and processor 114. In addition, this arrangement operates to exchange messages between a fitting system (such as the one described below with respect to FIG. 2) and processor 114 via processor 104. In other embodiments, other arrangements are possible as well.

Similar to memory sub-module 106, memory sub-module 116 may include one or more computer-readable storage media that can be read from, written to, or otherwise accessed by processor 114. In some embodiments, the storage media of the memory module 106 may also be read from, written to, or otherwise accessed by a fitting system, such as the fitting system described below with respect to FIG. 2. Additionally, the storage media of memory 106 may also be read from, written to, or otherwise accessed by one or more of the transmit/receive sub-module 112 and/or the control sub-module 118. In some embodiments, the storage media in the memory sub-module 116 may be configured to store configuration, or MAP, data for the hearing prosthesis 100 or other programming instructions that facilitate general operation of the hearing prosthesis 100 in accordance with the functions described herein. The storage media of the memory sub-module 116 may also be configured to store the results of one or more diagnostic tests that are initiated, performed, or otherwise controlled in whole or in part by either processor 114, control sub-module 118, or a fitting system.

Depending on the embodiment, hearing prosthesis 100 may include additional components that are not shown in FIG. 1. For example, in embodiments in which hearing prosthesis 100 is a cochlear implant, the cochlear implant may include an array of two or more electrodes. Typically, the electrodes are positioned along the recipient's cochlea. During operation, the stimulation module 111, in response to receiving one or more stimulation commands from the command module 100, applies via control sub-module 118 one or more electrical signals to the electrode array in order to stimulate the recipient's cochlea. However, as indicated above, depending on the embodiment, an electrode array, or other similar stimulation apparatus, may be positioned along other portions of the recipient, including for example the outer ear, inner ear, middle ear, cranial or facial bones, teeth, or brain stem.

Depending on the embodiment, control sub-module 118 includes circuitry configured to control and manage the electrode array or other similar stimulation apparatus. By way of example, such circuitry may include a signal generation sub-module, a transmit amplifier sub-module, a switching sub-module, a receive amplifier sub-module, and/or a signal measurement sub-module (not shown).

Example Fitting System

The effectiveness of a hearing prosthesis 100, and in particular, the command module 101 and stimulation module 111, typically depends not only on the design and capabilities of the device, but also on how well the device is configured for or "fitted" to a recipient. In some embodiments, the fitting of a hearing prosthesis 100, sometimes referred to as "programming" or "mapping," includes creating a set of configuration settings and other data that defines how the processor 104 of the command module 101 analyzes and converts audio signals received from the transducer 108 to output signals transmitted across data link 109 to the stimulation module 111. This configuration information is sometimes referred to as the recipient's "program" or "MAP." The recipient's "program" or "MAP" may be loaded into the prosthesis 100 via the data interface 102, 112 and stored in the data storage 106, 116 of the hearing prosthesis.

Figure 2:
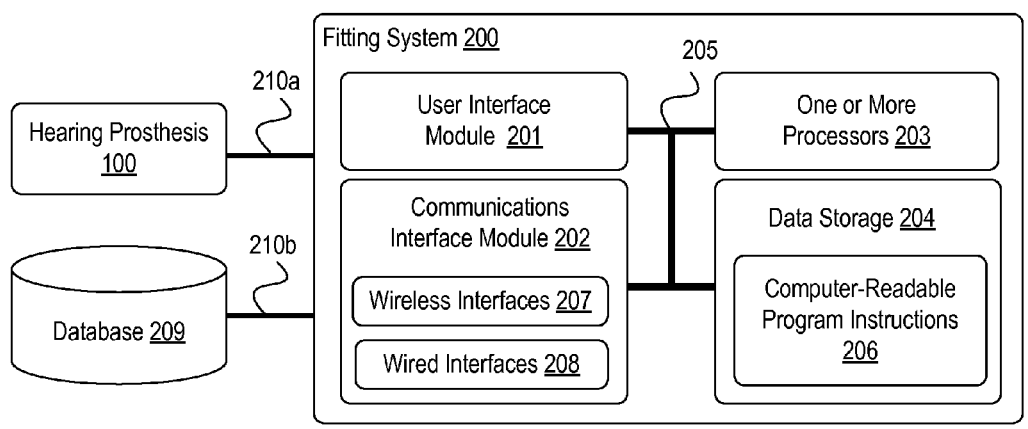
FIG. 2 shows a block diagram of a fitting system, according to one example embodiment.

FIG. 2 shows a block diagram of an example of a fitting system 200 that may be configured to execute fitting software for a particular hearing prosthesis and to load configuration settings to the memory 106 of the command module or memory 116 of the stimulation module via the prosthesis' data link 109. In the embodiment shown in FIG. 2, the fitting system 200 includes a user interface module 201, a communications interface module 202, one or more processors 203, and data storage 204, all of which may be linked together via a system bus or other connection circuitry 205. In other embodiments, fitting system 200 includes more, fewer, or different modules than those shown in FIG. 2.

In some embodiments, such as the one shown in FIG. 2, the user interface module 201 is configured to send data to and/or receive data from external user input/output devices such as a keyboard, a keypad, a touch screen, a computer mouse, a track ball, a joystick, and/or other similar devices, now known or later developed. In this embodiments, the user interface module 201 is also configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. Furthermore, in some embodiments, the user interface module 201 is configured to generate audible output(s), such as a speaker, speaker jack, audio output port, audio output device, earphones, and/or other similar devices, now known or later developed. Additionally, in some embodiments, the user interface module 201 includes or is communicatively coupled to an LCD or similar type of touch screen. The touch screen may be configured to display a user interface and/or to receive commands from a user.

As shown in FIG. 2, the communications interface module 202 includes one or more wireless interfaces 207 and/or wired interfaces 208 that are generally configurable to communicate with hearing prosthesis 100 via a communications connection 210a, to a database 209 via communications connection 210c, or to other computing devices (not shown). In some embodiments in which a hearing prosthesis contains a command module and a stimulation module, such as the embodiment depicted in FIG. 1, the fitting system is configured to communicate with both the command module and stimulation module via communications connection 210a. However, in some other embodiments in which a hearing prosthesis contains a command module and a stimulation module, the fitting system is configured to communicate with command module and any further communication to the stimulation module is carried out through the command module via data link 109. Other configurations are possible as well.

In some embodiments, the wireless interfaces 207 include one or more wireless transceivers, such as a Bluetooth transceiver, a Wi-Fi transceiver, a WiMAX transceiver, and/or other similar type of wireless transceiver configurable to communicate via a wireless protocol. In at least one embodiment, the wired interfaces 208 include one or more wired transceivers, such as an Ethernet transceiver, a Universal Serial Bus (USB) transceiver, or similar transceiver configurable to communicate via a twisted pair wire, a coaxial cable, a fiber-optic link or a similar physical connection.

In at least one embodiment, the one or more processors 203 include one or more general purpose processors (e.g., microprocessors manufactured by Intel or Advanced Micro Devices) and/or one or more special purpose processors (e.g., digital signal processors, application specific integrated circuits, etc.). In the embodiment depicted in FIG. 2, the one or more processors 203 are configured to execute computer-readable program instructions 206 that are contained in the data storage 204 and/or other instructions based on algorithms described herein.

The data storage 204 may include one or more computer-readable storage media that can be read or accessed by at least one of the processors 203. The one or more computer-readable storage media may include volatile and/or non-volatile storage components, such as optical, magnetic, organic or other memory or disc storage, which can be integrated in whole or in part with at least one of the processors 203. In some embodiments, the data storage 204 may be implemented using a single physical device (e.g., one optical, magnetic, organic or other memory or disc storage unit), while in other embodiments, the data storage 304 may be implemented using two or more physical devices.

In some embodiments, the data storage 204 includes computer-readable program instructions 206 and, in other embodiments, perhaps additional data. In some embodiments, for example the data storage 204 additionally includes program instructions that perform or cause to be performed at least part of the herein-described methods and algorithms and/or at least part of the functionality of the systems described herein.

Example Script Generation and Execution

In practice, different hearing prosthesis recipients use different configuration settings. This is usually the case because the configuration settings are tailored to the way in which the implant recipient's body responds to various applied stimulations. Typically, before a prosthesis recipient uses a hearing prosthesis (or other medical prosthesis, as the case may be), and perhaps at several milestones along the life of the hearing prosthesis, a trained professional conducts a fitting session. At a fitting session, the professional, such as an audiologist, conducts one or more tests to determine an appropriate set of configuration settings for the given hearing prosthesis and for the recipient.

By way of example, in embodiments in which the hearing prosthesis is coupled to an electrode array that is positioned in the recipient's cochlea, stimulation is carried out by applying an electrical signal between any two electrodes of the array in order to stimulate nerves in the recipient's cochlea. As described briefly above, during operation according to one embodiment, the command module 101, and more particularly, processor 104, analyzes an audio signal produced by transducer 108 in response to received sound waves and generates one or more stimulation commands for transmission to the stimulation module 111 across data link 109. Such a stimulation command usually identifies to the stimulation module 111 at least two electrodes between which to apply the electrical signal and the magnitude (e.g., current level) of that electrical signal. In another embodiment, however, the command module 101, analyzes an audio signal produced by transducer 108 and generates a preprocessed audio signal (in lieu of the stimulation commands) for transmission to the stimulation module 111 across data link 109. Other ways of generating stimulation are possible as well.

In any event, one example test that may be carried out during a fitting session in an embodiment such as the one described above is known as the Cochlear™ NRT® test. In some embodiments, the NRT test is generally used to determine how the recipient's cochlea, and perhaps other parts of the recipient's body, responds to various types of electrical stimuli. More particularly, during the NRT test, a stimulation module applies electrical signals of varying magnitude to different combinations of the electrodes that are placed in the recipient's cochlea. In addition, the stimulation module also conducts one or more physiological measurements of the cochlea and/or auditory nerve's response to each stimulation. Measurements such as these, along with perhaps visual and audible queues given by the recipient during or after the stimulation (or other information) serve as the basis for the audiologist or other entity to generate an appropriate set of configuration data. Operating according to an appropriate set of configuration data is advantageous because it reduces the risk that the recipient will experience damaging or injurious stimulation in relatively noisy sound environments. Furthermore, in some embodiments, this information also facilitates appropriate placement of electrodes within the recipient's cochlea. In addition to the NRT test, an audiologist or other entity can conduct any number of other tests or diagnostic exams, such as those that measure a recipient's blood pressure, pulse, ambient temperature, etc.

Tests, such as the NRT test or a set of NRT tests, are typically carried out by using a script. Generally, a script is program code (i.e., computer instructions designed to be executed by at least one processor) that dictates one or more actions for the hearing prosthesis to carry out. In some embodiments, scripts are generated by the audiologist and contain actions designed to facilitate tests carried out during fitting sessions. Scripts are usually stored at the fitting system 200 (e.g., in database 209 or data storage 204) and uploaded to the command module 101 when the test is ready to be conducted. Alternatively, scripts may be stored at the command module 101 (e.g., in memory 106) for easy recall.

In at least one embodiment, scripts are designed to be executed by the command module 101. However, as mentioned above, some tests, such as the NRT test, involve the stimulation module applying stimulation and measuring a response. Therefore, at least a portion of the instructions that make up the script indicate to the command module 101 to intermittently transmit instructions to the stimulation module 111 via the data link 109.

Figure 3:
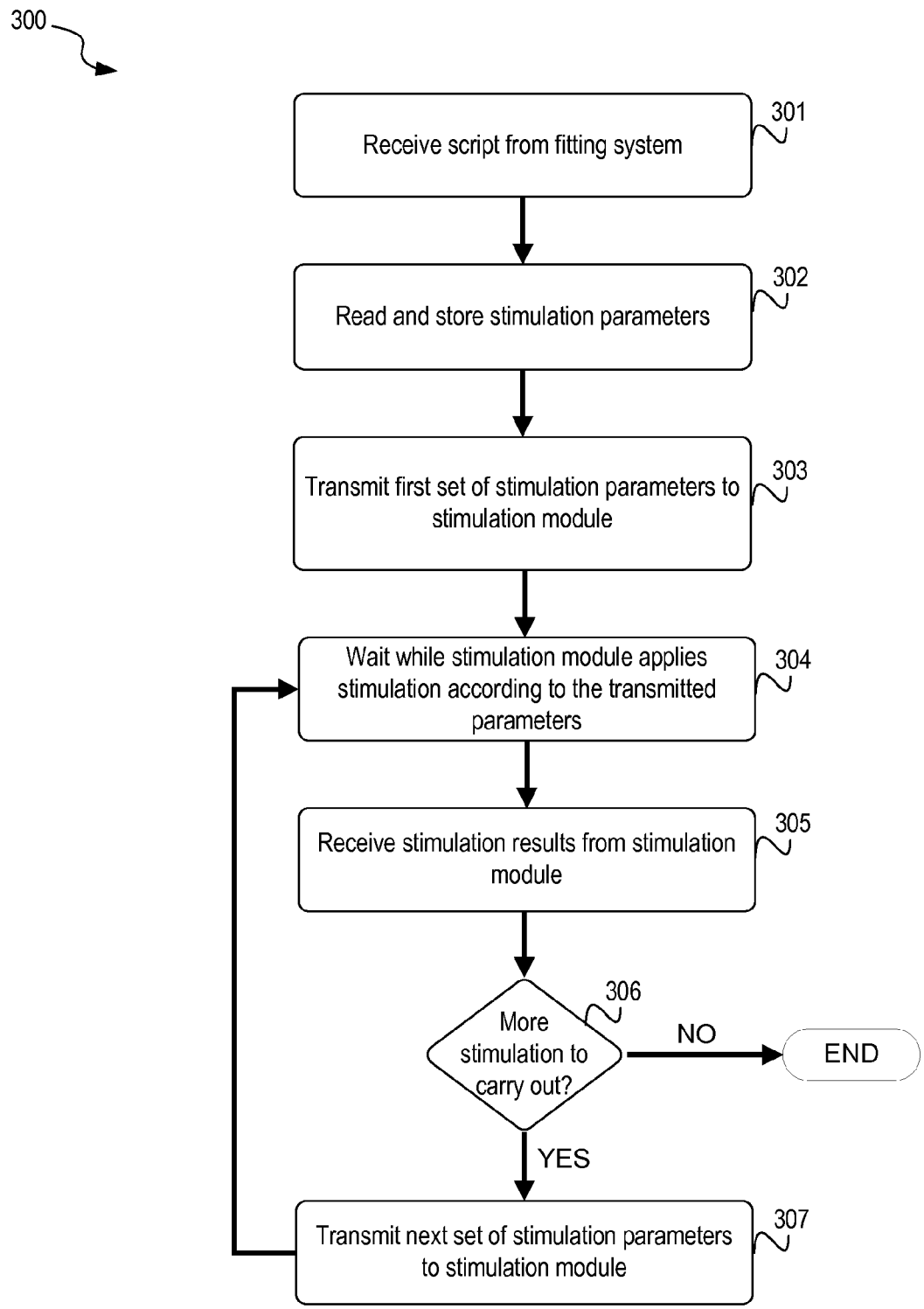
FIG. 3 is a flow chart depicting an example method for receiving and executing a script, according to one example embodiment.

FIG. 3 is a flowchart depicting an example method 300 for receiving and executing an example NRT script during a fitting session (or at some other time). The method 300 may be executed by one or more of the sub-modules of command module 101, such as processor 104. Method 300 begins at block 301 where the command module 101 receives the script from the fitting system 200. In one embodiment, the fitting system 200 retrieves the script from database 209 and uploads it to the command module via communications connection 210a. Alternatively, in some embodiments the command module 101 has already stored the script in memory 106; thus, at block 301, the command module simply retrieves the script from memory 106.

At block 302, the command module 101 begins execution of the example script by reading and storing the stimulation parameters. In the example embodiment depicted by FIG. 3, the script dictates for the stimulation module to apply one or more stimulations and record the response. The parameters for these stimulations (e.g., to which electrodes to apply electrical signals, the order in which to apply them, the magnitude at which they are applied, etc.) are specified in the script. Once the script is received, the command module 101 reads these parameters and perhaps stores them in memory 106 so that the command module 101 can eventually transmit the parameters to the stimulation module 111.

Execution of the script continues at block 303 where the command module 101 transmits the first set of stimulation parameters to the stimulation module 101. In one embodiment, these parameters are transmitted to the stimulation module 111 via the data link 109 in the form of a stimulation command. As indicated above, a stimulation command generally instructs the stimulation module 111 to apply an electrical signal between two or more electrodes at a particular magnitude. However, in other embodiments, the parameters are transmitted to the stimulation module 111 in other forms.

Continuing at block 304, after the first set of stimulation parameters are transmitted to the stimulation module 111, the command module 101 waits while the stimulation module 111 applies the stimulation in accordance with the transmitted parameters. In one embodiment, the script dictates for the command module to wait a predetermined amount of time before proceeding to the next instruction in the script. In at least one embodiment, the predetermined amount of time is an estimate of how long it will take for the stimulation module 111 to receive the stimulation parameters, apply the stimulation, and measure any response.

The method 300 continues at block 305, where the command module receives the results of the previous stimulation. As indicated above, in response to receiving a set of stimulation parameters, the stimulation module 111 applies stimulation in accordance with those parameters. The stimulation module 111 also measures a response to the applied stimulation, which, as mentioned above, can take the form of measuring a physiological response of the recipient's auditory nerve to the applied stimulation. In at least one embodiment, this measurement is returned to the command module 101 via data link 109 and in turn, to the fitting system 200 for analysis by an audiologist or other entity.

Continuing at block 306, the command module 101 makes a determination of whether there are more stimulations to carry out. If there are no more stimulations to carry out, execution of the script ends. However, if there are more stimulations to carry out, flow proceeds to block 307 where the command module 101 transmits the next set of stimulation parameters to the stimulation module 111. From block 307, flow proceeds back to block 304 where the command module again waits while the stimulation module 111 applies the stimulation in accordance with the most recently transmitted parameters.

The script execution approach described by the example method 300 is referred to as the "master-slave" approach. For example, the command module 101 is referred to as the master, whereas the stimulation module 111 is referred to as the slave. The master is the entity that executes the script. When it is desired for the slave to carry out one or more actions, the master instructs the slave to carry out the desired actions. As a result, the master-slave approach tends to be somewhat slow, which may be undesirable in some circumstances. Moreover, this approach is somewhat problematic because of the frequent communications back and forth between the master and the slave.

Typically, for example, the command module will attempt to execute instructions simultaneously with the stimulation module executing instructions. However, the command module does not know the precise time that the stimulation module will receive its instructions from the command module. Thus, sometimes, the command module will begin executing instructions too early or too late. Further, the command module also does not know the precise time that the stimulation module finishes stimulation and is ready to transmit back a measured response. Moreover, in some embodiments, it is desired for the command module to cease all radio-frequency (RF) communication (to the stimulation module or otherwise) while the stimulation module is measuring a response to applied stimulation. Depending on the type of stimulation, RF communication causes noise to be perceived by in the cochlea, and more particularly by the electrodes placed within the cochlea, which in turn can cause an erroneous measurement. Therefore, scripts are typically designed such that the command module will wait a predetermined amount of time before checking to see if the stimulation module has transmitted a response and transmitting the next set of stimulation parameters. If this predetermined amount of time is not accurate, then the command module may interfere with the stimulation module's measurement.

Another script execution approach is referred to as a "peer" approach. In the peer approach, the fitting system (or another entity) generates two versions of a script: one for the command module, and one for the stimulation module. Each script generally includes instructions pertinent to a specific module. And each module executes its respective script at about the same time. In some embodiments, the peer approach reduces the amount of communication between the two modules and thus reduces the chance of errors and interference.

In one embodiment, the command module script and the stimulation module script are substantially the same script; however, during execution, the command module only executes instructions that pertain to the command module, and the stimulation module only executes instructions that pertain to the stimulation module. In another embodiment, the command module script and the stimulation module script are different scripts. In such an embodiment, the command module script contains only those instructions that pertain to the command module, and the stimulation module only contains those instructions that pertain to the stimulation module. Other configurations of command module scripts and stimulation module scripts are possible as well.

As a general matter, the command module script and the stimulation module script typically contain instructions that cause the command module and the stimulation module to perform actions in a synchronized manner. As mentioned above, one example of the command module and the stimulation module performing actions in a synchronized manner is the command module ceasing RF transmission during the time that the stimulation module is measuring a response to applied stimulation. Another example of synchronized actions is the command module generating a pulse for an external device during the time that the stimulation module is applying stimulation. Still other synchronized actions are possible as well.

Figure 4:
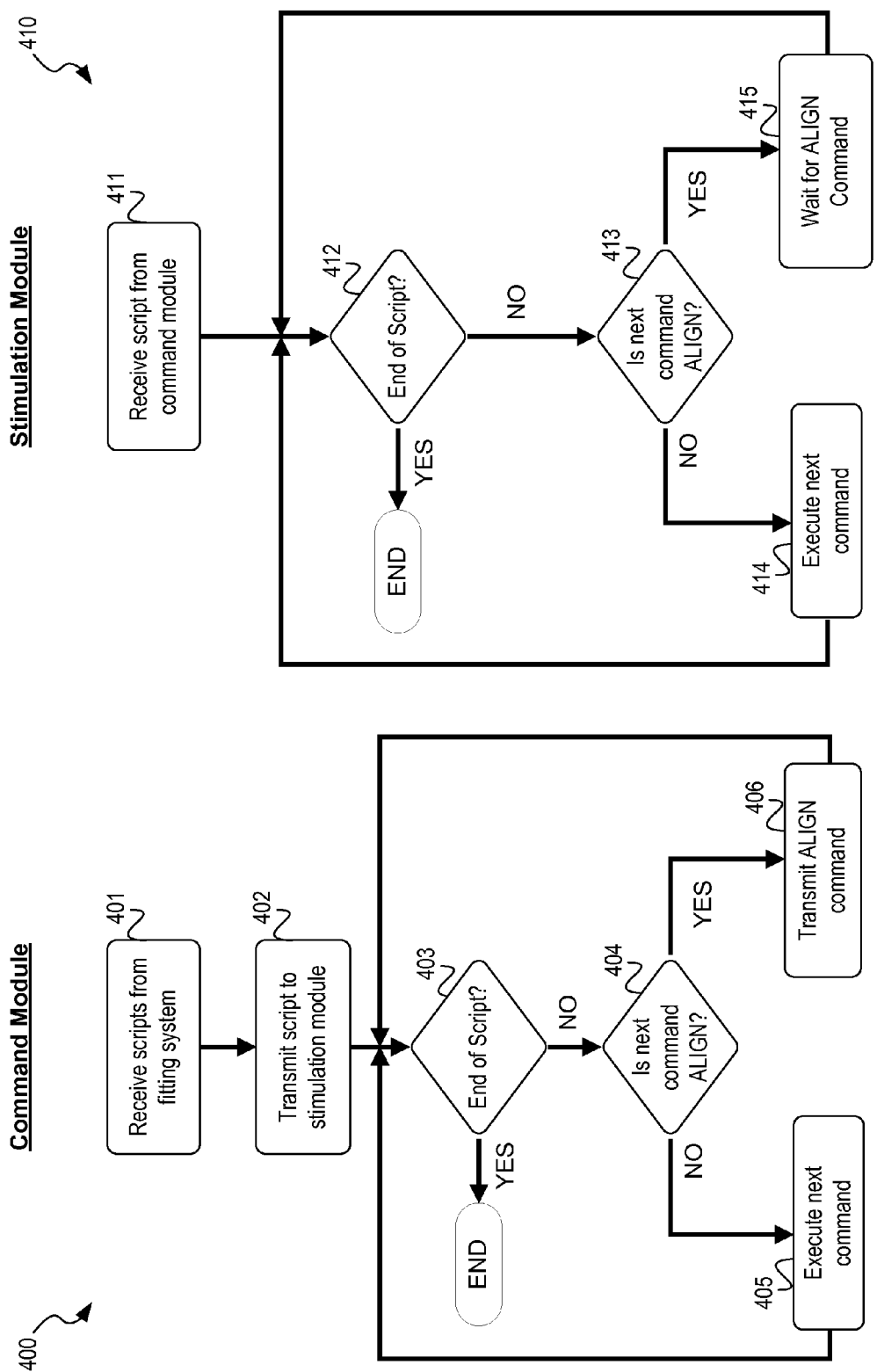
FIG. 4 is a flow chart depicting an example method for receiving and simultaneously executing a script, according to another example embodiment.

FIG. 4 shows two flowcharts 400, 410, depicting the simultaneous execution of two example NRT scripts, one by the command module and one by the stimulation module. Receipt and execution of a command module script (by the command module 101) is depicted by method 401, whereas receipt and execution of a stimulation module script (by the stimulation module 111) is depicted by method 410. As those skilled in the art will understand, the methods 400 and 410 are merely depictions of the execution of example scripts, and other types of scripts are possible as well, as are other methods of simultaneously executing two scripts.

Method 400 may be executed by one or more sub-modules of command module 101, such as processor 104. Method 400 begins at block 401 where the command module 101 receives two scripts from the fitting system 200. In one embodiment, at this block the command module 101 receives a command module script and a stimulation module script. In some embodiments, the fitting system retrieves the scripts from database 209 and uploads them to the command module 101. Alternatively, in some embodiments, the command module has already stored one or more of the scripts in memory 106; thus at block 401, the command module simply retrieves the scripts from memory 106.

At block 402, the command module transmits the stimulation module script to the stimulation module 111. For example, in some embodiments, the command module transmits the script across data link 109 to the stimulation module. Alternatively, in embodiments in which the stimulation module has already received a script (or is otherwise provisioned with a script), this block is skipped.

After block 402 but before block 403, the command module begins execution of the script. At block 403, the command module makes a determination of whether the script is completed. If the script is completed, the flow ends. However, if the script is not completed, the execution continues at block 404 where the command module determines whether the next command is an ALIGN command. If the next command is not an ALIGN command, the execution continues at block 405 where the command module executes the next script command.

However, at block 404 if the command module determines that the next command is an ALIGN command, the execution continues at block 406 where the command module transmits an align command to the stimulation module. ALIGN commands are typically used before certain time-sensitive portions of a script are executed. In some embodiments, ALIGN commands are used in order for the two modules to execute certain actions at substantially the same time.

For example, as will be described below with respect to flow diagram 410, in some embodiments there are certain instructions included in a stimulation module script that instruct the stimulation module to pause execution of the script. In such embodiments, an ALIGN command transmitted by the command module is generally any message that indicates to the stimulation module to resume execution of its script. Other examples of ALIGN commands are possible as well.

After execution of block 405 or block 406, execution continues back at block 403 where the command module again determines whether the script is completed. Upon completion of the script, the command module will usually receive measurements or other test result data from the stimulation module.

Notably, in this embodiment, aside from the initial transmission of the stimulation module script, the command module does not have to transmit a set of stimulation parameters to the stimulation module before each stimulation. Furthermore, because the scripts take advantage of ALIGN commands, the command module and stimulation module are able to compensate for small differences in the speed with which each module executes its script. For example, for one reason or another (typically because of inaccuracies in the system clocks), one module may execute its script faster than the other module. However, by way of the align command, one module that reaches a critical point faster than the other module will pause its execution until the other module catches up. Other uses of align commands are possible as well.

Referring now to method 410, this method may be executed by one or more sub-modules of stimulation module 111, such as processor 114. Method 410 begins at block 411 where the stimulation module receives the stimulation module script from the command module 101 across data link 109. Alternatively, in some embodiments, the stimulation module has already stored a script in memory 116; thus, at block 411 the stimulation module may retrieve the stimulation module script from memory 116.

At block 412, the stimulation module makes a determination of whether the script is completed. If the script is completed, the flow ends. However, if the script is not completed, the execution continues at block 413 where the stimulation module determines whether the next command is an ALIGN command. If the next command is not an ALIGN command, the execution continues at block 414 where the stimulation module executes the next script command. In some embodiments, the command executed at block 414 is a command that instructs the stimulation module to apply stimulation in accordance with a set of stimulation parameters indicated in the stimulation module script. In at least one embodiment, these parameters indicate a particular electrode to apply an electrical signal and a magnitude of that signal. In at least one embodiment, these parameters may indicate other things, such as the shape or pattern of the electrical signal (e.g., a pulse, square wave, etc.), the duration of the signal, etc. Other parameters and examples of commands to execute at block 414 are possible as well.

Referring back to block 413, if the stimulation module determines instead that the next command is an ALIGN command, the execution continues at block 415 where the stimulation module pauses execution of the script and waits for an ALIGN command from the command module. Once the stimulation module receives an ALIGN command from the command module, which, as described above, is generally any message that indicates to the stimulation module to resume execution of its script, the execution resumes at block 412 where the stimulation module again determines whether the script is completed. Upon completion of the script, the stimulation module will usually transmit measurements or other test-result data to the command module.

FIG. 4 depicts one example method that utilizes ALIGN commands; however, other examples of using ALIGN commands are possible as well. For instance, in one embodiment, ALIGN command functionality that was described above as being carried out by the command module is instead carried out by the stimulation module. Likewise, ALIGN command functionality that was described above as being carried out by the stimulation module is instead carried out by the command module. In such an embodiment, when the command module encounters an ALIGN command in the command module script, it will pause execution of the command module script and wait for receipt of an ALIGN command from the stimulation module. And when the stimulation module encounters an ALIGN command in the stimulation module script, it will transmit an ALIGN command to the command module. Still other examples of utilizing ALIGN commands are possible in other embodiments.

In addition, although FIG. 4 depicts an example method for simultaneously executing two NRT scripts, those skilled in the art understand that the NRT test is merely one example test and generally, any type of test or series of actions, whether conducted during a fitting session or otherwise, can utilize the peer approach for dual script execution as well as ALIGN command functionality.

Figure 5:
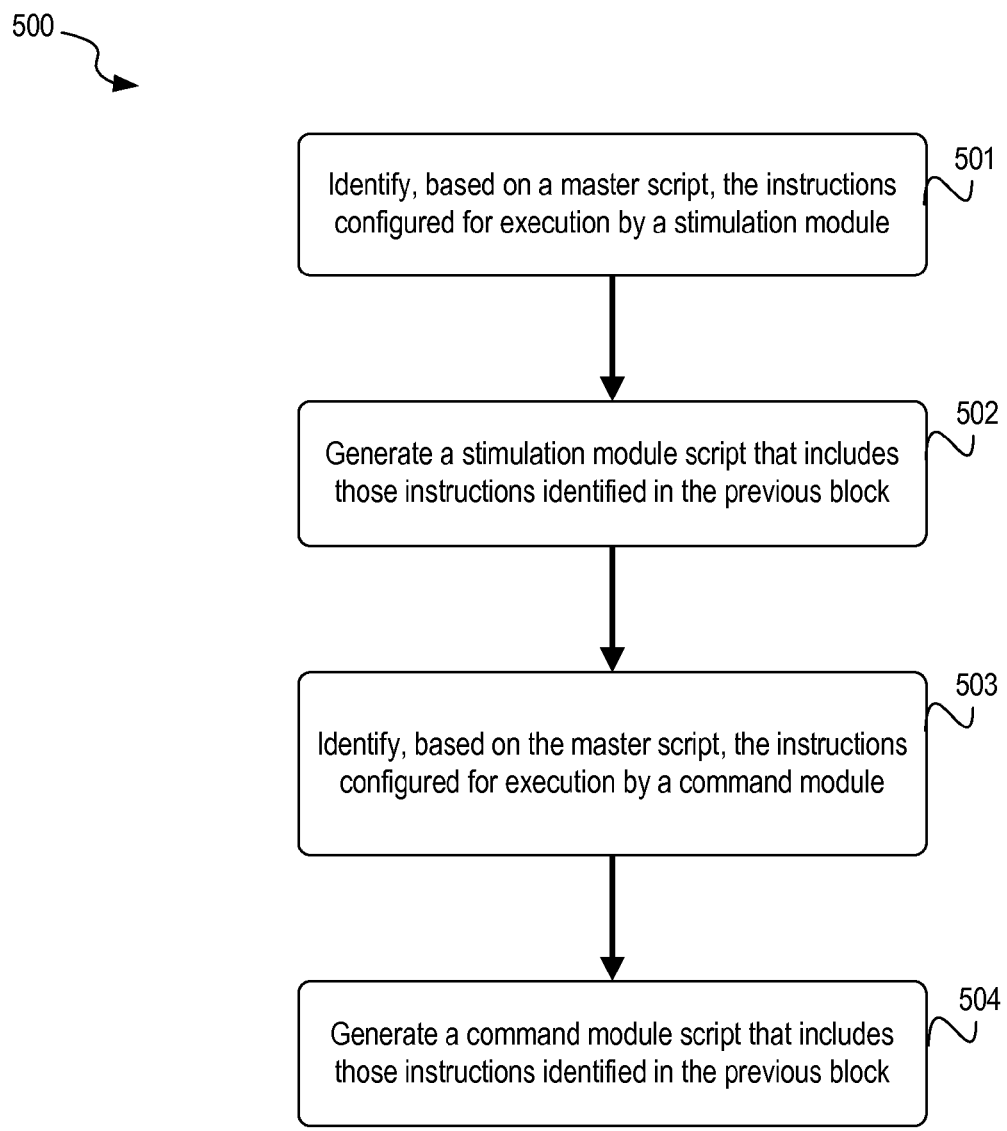
FIG. 5 is a flow chart depicting an example method for generating two scripts, according to an example embodiment.

FIG. 5 is a flow chart depicting an example method for generating two scripts. Method 500 is described as being carried out by a sub-module of fitting system 200, such as the one or more processors 203; however, method 500 can be carried out by any other entity as well. Method 500 begins at block 501 where the fitting system 200 identifies, based on a master script, instructions configured for execution by a stimulation module. In one embodiment, instructions configured for execution by the stimulation module take the form of those instructions that the command module transmits to the stimulation module during the execution of the master script. In other embodiments, the instructions configured for execution by the stimulation module are identified based on what the instruction is asking the module to do and the capabilities of each module. For example, typically, the stimulation module is the only module that can physically apply electrical signals to the electrode array. Thus, when the fitting system analyzes a master script and encounters an instruction that only the stimulation module can carry out (e.g., an instruction to apply stimulation), the fitting system identifies that instruction as one configured for execution by the stimulation module. Other ways of identifying instructions that are configured for execution by the stimulation module are possible as well.

Proceeding to block 502, the fitting system generates a stimulation module script that includes those instructions identified at block 501. Generally, the stimulation module script can be of any type and format able to be executed by the stimulation module.

At block 503, the fitting system identifies, based on a master script, instructions configured for execution by a command module. In one embodiment, instructions configured for execution by the stimulation module take the form of those instructions that are designed for only the command module to execute (i.e., and not transmit to the stimulation module). In other embodiments, the instructions configured for execution by the command module are identified based on what the instruction is asking the module to do and the capabilities of each module. For example, in some embodiments, the command module is the only module that can directly communicate with the fitting system. Thus, when the fitting system analyzes a master script and encounters an instruction that only the command module can carry out (e.g., an instruction to transmit data to the fitting system or receive data from the stimulation module), the fitting system identifies that instruction as one configured for execution by the command module. Other ways of identifying instructions that are configured for execution by the command module are possible as well.

Finally, at block 504, the fitting system generates a command module script that includes those instructions identified at block 503. Generally, the command module script can be of any type and format able to be executed by the stimulation module. Other ways of generating two scripts based on a master script are possible as well.

Example Timing Diagram

Figure 6:
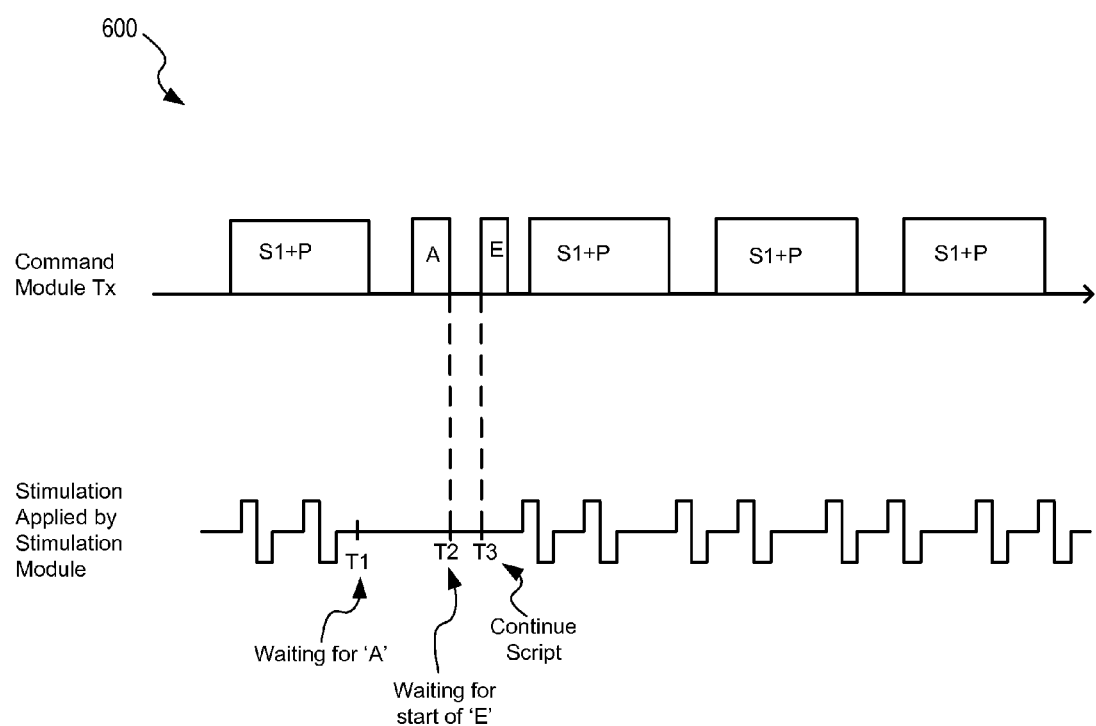
FIG. 6 is an example timing diagram, according to an example embodiment.

FIG. 6 shows a timing diagram 600 that depicts an example implementation of the ALIGN command functionality. As depicted in the timing diagram 600, the command module transmits packets to the stimulation module. In this embodiment, the packets contain two slots. The first slot is usually reserved for instructions for the stimulation module. The second slot is usually reserved for ALIGN commands. In other embodiments, packets contain more or fewer slots, each of which is reserved for different types of data. As shown in the embodiment depicted by FIG. 6, the command module transmits several packets containing slot one data and power data, labeled "S1+P." Power data, in one embodiment, is dummy-data designed to provide power to the stimulation module via the transcutaneous data link.

As further shown in the embodiment depicted in FIG. 6, the stimulation module executes a stimulation module script and applies stimulation to an array of electrodes. At time T1, the stimulation module encounters an ALIGN command in the script and therefore pauses execution of the script and waits for an ALIGN command from the command module. Meanwhile, the command module also encounters an ALIGN command in the command module script and therefore transmits a small RF message, labeled 'A.' The 'A' packet only has data in slot two, which as mentioned above with respect to one embodiment, is reserved for ALIGN commands. At time T2, the stimulation module receives the 'A' message and waits for the beginning of the next received packet, labeled 'E.' At time T3, the command module transmits the 'E' packet, which in some embodiments is an empty packet. As soon as the stimulation module receives the 'E' packet, (e.g., shortly after the command module transmits the 'E' packet), the stimulation module resumes execution of the script, as depicted in FIG. 6. This is one example embodiment that utilizes ALIGN command functionality; however, embodiments that utilizes ALIGN functionality in other ways are possible as well.

Computer Readable Media Implementations

In some embodiments, the disclosed features and functions of the systems, methods, and algorithms shown and described herein may be implemented as computer program instructions encoded on a computer readable media in a machine-readable format.

FIG. 7 shows an example of an article of manufacture 700 including computer readable media with instructions for causing one or more processors to execute peer approach to script execution, according to some embodiments of the disclosed systems and methods. FIG. 7 shows a schematic illustrating a conceptual partial view of an example article of manufacture 700 that may include computer program instructions 702 for executing a computer process on a computing device, arranged according to at least some embodiments described herein.

In some examples, the article of manufacture 700 may include a computer-readable medium 703, such as, but not limited to, a hard disk drive, a Compact Disc (CD), a Digital Video Disk (DVD), a digital tape, flash memory, etc. In some implementations, the article of manufacture 700 may include a computer recordable medium 704, such as, but not limited to, a hard disk drive, a Compact Disc (CD), a Digital Video Disk (DVD), a digital tape, flash memory, etc.

The one or more programming instructions 702 may be, for example, computer executable and/or logic implemented instructions. In some embodiments, processor 104 of command module 101 or processor 114 of stimulation module 111, alone or in combination with one or more other processors associated with the hearing prosthesis 100, may be configured to perform various operations, functions, or actions to implement the features and functionality of the disclosed systems and methods based at least in part on the programming instructions 702.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising,
    at a medical prosthesis, receiving at least two scripts, wherein each of the at least two received scripts defines a set of instructions to be carried out by the medical prosthesis;
    simultaneously executing the at least two received scripts; and
    periodically synchronizing execution of the at least two scripts, wherein periodically synchronizing the execution of the at least two scripts comprises pausing the execution of one of the at least two scripts while continuing the execution of another of the at least two scripts.

2. The method of claim 1,
    wherein the medical prosthesis comprises a first module and a second module each configured to transmit and receive data across a data link,
    wherein simultaneously executing the at least two scripts comprises executing a first script by the first module and simultaneously executing a second script by the second module.

3. The method of claim 2, wherein the first script includes different instructions than the second script.

4. The method of claim 1, wherein
    the set of instructions included in the first script are substantially equivalent to the set of instructions included in the second script,
    executing the first script comprises executing a subset of instructions included in the first script that is designated for the first module, and
    executing the second script comprises executing a subset of instructions included in the second script that is designated for the second module.

5. The method of claim 2, wherein pausing execution of one of the at least two scripts comprises pausing execution of the second script at a point in which the second script indicates to receive an align message, and wherein continuing the execution of another of the at least two scripts comprises:
    continuing execution of the first script while the second script is paused, wherein the first script includes instructions for transmitting the align message to the second module; and
    in response to executing the instructions for transmitting the align message, transmitting, by the first module, the align message to the second module.

6. The method of claim 5, further comprising:
    receiving the align message at the second module while execution of the second script is paused; and
    in response to the receiving of the align message, resuming execution of the second script by the second module.

* * * * *